United States Patent [19]

Aulhorn et al.

[11] 4,403,842
[45] Sep. 13, 1983

[54] APPARATUS FOR TESTING TWILIGHT VISION AND BLINDING SENSITIVITY

[75] Inventors: Elfriede Aulhorn, Tuebingen; Jakob Kocher, Dusslingen; Josef Reiner, Rodenkirchen, all of Fed. Rep. of Germany

[73] Assignee: Oculus Optikgeraete GmbH, Dutenhofen, Fed. Rep. of Germany

[21] Appl. No.: 318,242

[22] Filed: Nov. 4, 1981

[51] Int. Cl.³ .............................................. A61B 3/02
[52] U.S. Cl. .................................... 351/237; 351/243
[58] Field of Search ............... 351/233, 234, 235, 236, 351/237, 243, 245

[56] References Cited

U.S. PATENT DOCUMENTS 3,415,594 12/1968 Aulhorn et al. .................... 351/237

Primary Examiner—John K. Corbin
Assistant Examiner—Rodney B. Bovernick
Attorney, Agent, or Firm—Flynn, Thiel, Boutell & Tanis

[57] ABSTRACT

An apparatus for testing twilight vision and blinding sensitivity includes a housing having openings in opposite sides thereof, a person to be tested being able to look through the housing along a line of sight extending through both openings. A filter is provided for one of the openings to limit external light entering such opening. A concave mirror is arranged in the housing with its optical axis normal to the line of sight, and a semitransparent mirror is arranged at the intersection of and at 45° angles with respect to the line of sight and the mirror optical axis. A screen arranged at the focal point of the mirror is simultaneously illuminated by two projectors, a test figure being arranged in the beam of one projector and the light intensities of the two projectors being inversely proportionally controlled. Two filters are provided which can each be inserted in the beam of a respective one of the projectors to further reduce the light intensity. A headlight simulating source is arranged adjacent the field of vision on the screen and a third projector projects at least one fixation point onto the screen.

6 Claims, 6 Drawing Figures

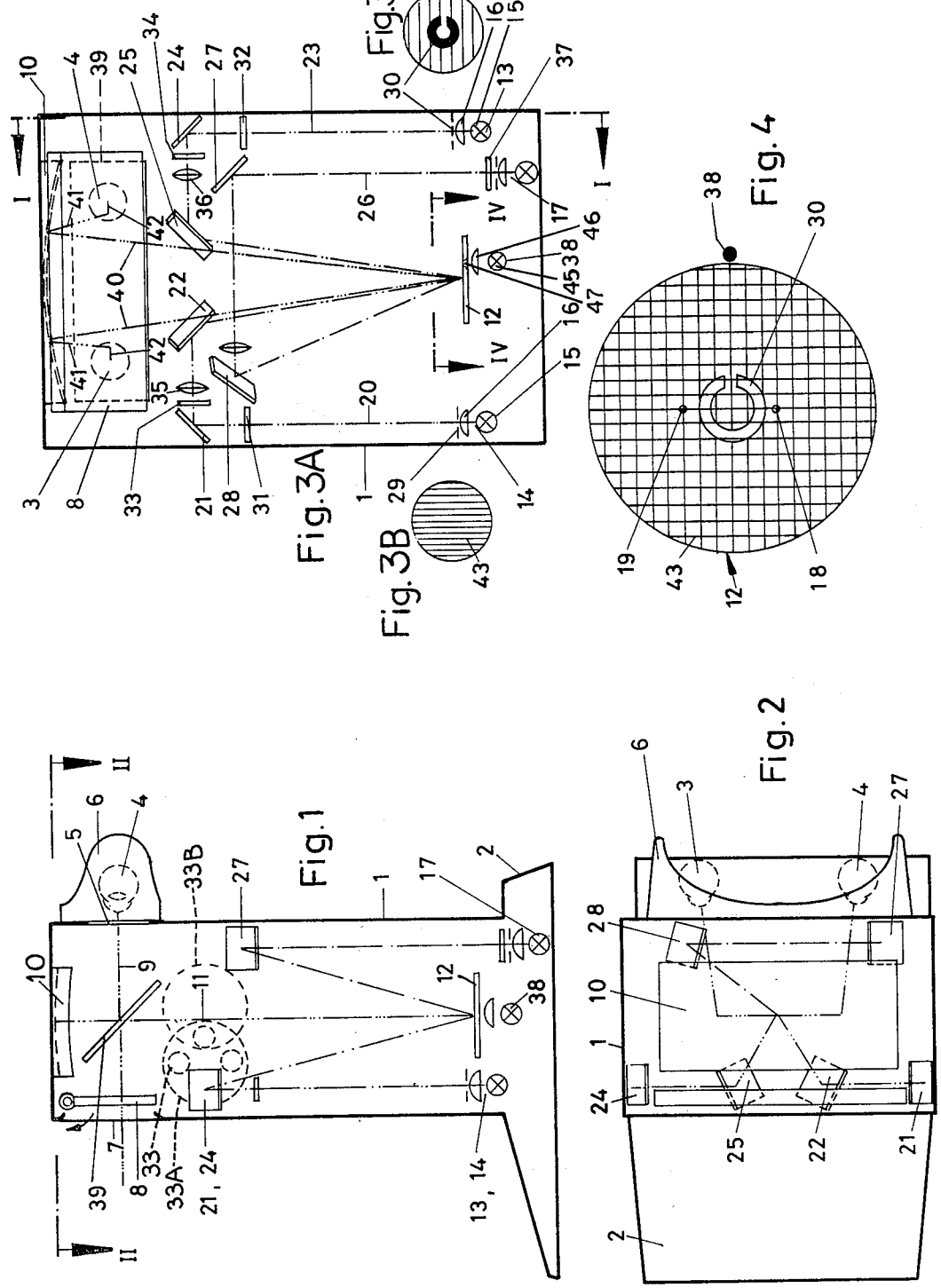

APPARATUS FOR TESTING TWILIGHT VISION AND BLINDING SENSITIVITY

FIELD OF THE INVENTION

The invention relates to an apparatus for testing a person's twilight vision and blinding sensitivity and, more particularly, to such an apparatus which includes a screen illuminated simultaneously by two projectors, a test figure being arranged in the beam of one projector and the light intensities from both projectors being controlled with respect to one another so that the light intensity from one projector increases in the same degree as the intensity from the other projector is reduced, and includes a headlight source arranged next to the field of vision on the screen.

BACKGROUND OF THE INVENTION

An apparatus of the above-mentioned type is known from German Pat. No. 1 282 847. This apparatus serves to measure twilight vision, blinding sensitivity, and adaptation capability. Measuring these characteristics is particularly important for vehicle drivers. However, testing them with the conventional apparatuses is relatively expensive, since such testing must take place in a totally dark room and the person being tested must be 3 meters away from the screen.

The basic purpose of the invention is to construct an apparatus of the above-mentioned type with which the testing can be carried out in a normally illuminated room and the distance of the tested person from the screen can be kept sufficiently small so that the screen and the projectors can all be arranged in a compact apparatus.

SUMMARY OF THE INVENTION

This purpose is attained inventively by providing an apparatus of the foregoing type in which the screen is arranged at the focal point of a concave mirror, a semi-transparent mirror inclined with respect to the optical axis of the concave mirror is arranged between the concave mirror and the screen, which semi-transparent mirror is aligned with the eyes of the tested person, and an opening is provided in the apparatus along the sight line of the eyes of the tested person which permits an unhindered looking out, the opening being provided with a filter for weakening the light entering the apparatus from outside.

Thus, the tested person looks completely through the testing apparatus so that, during testing, influences from a convergence caused by the apparatus and an accommodation do not take place. On the other hand, the test figure and the outer field are blended into the field of view of the tested person by the semi-transparent mirror. Since the screen is at the focal point of the concave mirror, the tested person sees the test figure at infinity. The distance of the screen from the concave mirror can, however, be kept small, so that the inventively constructed apparatus has only small dimensions.

BRIEF DESCRIPTION OF THE DRAWINGS

One exemplary embodiment of the invention is described in greater detail hereinafter in connection with the drawing, in which:

FIG. 1 is a schematic sectional side view taken along the line I—I of FIG. 3 of an apparatus embodying the present invention;

FIG. 2 is a sectional view taken along the line II—II of FIG. 1;

FIG. 3A is a schematic sectional rear view of the apparatus illustrated in FIG. 1;

FIGS. 3B and 3C illustrate patterns projected onto a screen in the apparatus of FIG. 1; and FIG. 4 is a view taken along the line IV—IV of FIG. 3A.

DETAILED DESCRIPTION

Referring to FIGS. 1 and 2, the apparatus for testing twilight vision and blinding sensitivity includes a housing 1 which is provided with a base 2. The person being tested, whose two eyes 3 and 4 are illustrated with broken lines, looks through an opening 5 into the housing 1 along a sight line 9. To shield against external light influences, a cover 6 which reaches over the eyes 3 and 4 is provided. Directly opposite the opening 5 is a further opening 7 in the housing 1. A conventional and pivotally supported filter 8 can be swung into this opening in order to reduce the intensity of the light which comes from outside. The filter 8, moreover, is transparent, so that the tested person can look unhindered through the apparatus to the outside.

Arranged perpendicular to the sight line 9 is the optical axis 11 of a concave mirror 10. A screen 12 is arranged at the focal point of the concave mirror 10, which screen is illuminated by two projectors 13 and 14 (FIG. 3A) which each have a lamp 15 and a condensing lens 16.

A further projector 17 is also arranged in the housing 1, and serves to project two fixation points 18 and 19 onto the screen 12. These fixation points are illustrated in FIG. 4.

Referring to FIG. 3A, two conventional mirrors 21 and 22 are arranged to deflect the beam 20 of the projector 14, which mirrors deflect the light of the projector 14 onto the screen 12. These mirrors are needed so that the projector 14 can be built with a relatively low height, but so that an influence of the beams of the various projectors does not occur. For the same reason, two conventional mirrors 24 and 25 are arranged to deflect the beam 23 of the projector 13 and two conventional mirrors 27 and 28 to deflect the beam 26 of the projector 17.

More specifically, the beams 23, 20 and 26 travel upwardly from the lamps of the respective projectors 13, 14 and 17 to the respective angled mirrors 24, 21 and 27, are deflected by the mirrors 24, 21 and 27 and travel horizontally to the respective angled mirrors 25, 22 and 28, and are deflected by the mirrors 25, 22 and 28 and travel generally downwardly to the screen 12. If desired, any or all of the mirrors 21, 22, 24, 25, 27 and 28 could be replaced with conventional deflecting prisms.

A plate 29 having a circular aperture is arranged in front of the projector 14, while a plate having a circular aperture and a test figure 30 supported in the aperture is arranged in front of the projector 13. The test figure 30 is illustrated in FIG. 3C. The circle illustrated in FIG. 3B is supposed to indicate that the projector 14 sends out only light of an ascertainable identity. The vertical lines in FIGS. 3B and 4 indicate that the projector 14 illuminates the area of the screen 12 corresponding to both the test figure 30 and the outer field identified with reference numeral 43, while the horizontal lines in FIGS. 3C and 4 indicate that the projector 13 illuminates only the area of the screen 12 corresponding to the outer field 43.

Filters 31 and 32 (FIG. 3A) are arranged in the beams 20 and 23 of the projectors 14 and 13, which filters are selected to correspond to one another in such a manner that the combined light intensity from the projectors 13 and 14 which reaches the screen 12 is always a constant. If the light intensity from the projector 14 is increased, then the light intensity from the projector 13 is reduced accordingly. Variation of the light intensities from the two projectors in eight discrete steps is sufficient, and so the filters 31 and 32 need only be changed accordingly.

Further filters 33 and 34 can be inserted adjacent each of the mirrors 21 and 24 in the beams 20 and 23, respectively, which filters are conventional and effect a further reduction of the light intensity. These two filters are used when, for example, the difference between a wet road and a dry road is supposed to be simulated for the tested person.

If desired, several of the filters 33, each of which reduces the light beam intensity by a different degree, can be supported at peripherally spaced locations in a disk 33A which is indicated in broken lines in FIG. 1. The disk 33A is supported in a conventional manner for rotation about a horizontal axis so that a selected one of the filters 33 can be moved into alignment with the light beam, and is supported in a conventional manner for horizontal movement to a position 33B in which no filter 33 is disposed in the light beam. A similar, not illustrated disk can be provided to support a plurality of the filters 34 in a similar manner, and is preferably coaxial with and coupled to the disk 33A by a common shaft so that variation of the filters 33 and 34 is effected in a simultaneous, synchronized manner. When a plurality of the filters 31 and 32 are provided, they can be mounted in not illustrated disks in a similar manner, and these disks can also, if desired, be mechanically coupled for simultaneous, synchronized rotation.

Furthermore, projecting lenses 35 and 36 are respectively provided in the beams 20 and 23, which lenses are needed for properly projecting images on the screen 12 and are parts of the projectors 13 and 14.

With the help of the projector 17 and a suitable template 37 located in front of the projector 17, fixation points 18 and 19 are projected onto the screen 12 and are intended to facilitate the alignment of the eyes 3 and 4 of the tested person so that, when the headlight simulating source 38 is switched on, the tested person does not accidentally look directly into the headlight source 38. The headlight source 38 includes, in a conventional manner, a lamp 45, a condenser lens 46 and an aperture 47 in the screen 12. If desired, the projector 17 can be constructed so that the intensity of its beam can be varied in a conventional manner, for example by connecting a conventional, not illustrated potentiometer in series with the lamp 45.

A conventional semi-transparent mirror 39 is inserted into the optical axis 11 of the concave mirror 10 at an angle of 45° with respect to the optical axis 11 and the sight line 9 of the eye of the viewer. The concave mirror 10 causes the image which is projected onto the screen 12 to appear at infinity. The image is deflected by the semi-transparent mirror 39 to the eyes of the tested person, as shown by the broken lines 40, 41 and 42.

In other words, the semi-transparent mirror 39 is located at the intersection of and is inclined at 45° with respect to the mirror optical axis 11 and the line of sight 9. The reflective surface of the mirror 39 is the upper side thereof. Light projected onto the screen 12 passes upwardly through the mirror 39, reaches and is reflected downwardly by the mirror 10, and is then reflected to the eyes 3 and 4 of the person being tested by the upper surface of the mirror 39. Light entering the apparatus through the opening 7 and filter 8 can pass through the mirror 39 along the line of sight 9 to the eyes 3 and 4 of the person being tested.

By simultaneously replacing the filters 31 and 32 provided in the beams 20 and 23, the contrast of the outer field 43 with respect to the test figure 30 can be changed. The test figure 30, in the exemplary embodiment, is a Landolt ring. Through this, twilight vision can be tested. For the simulation of a wet and a dry street the filters 33 and 34 can also be inserted and removed into the beams 20 and 23. To test blinding sensitivity, the headlight source 38 arranged next to the test figure 30 on the screen 12 is switched on for a short time.

The inventively constructed apparatus for testing twilight vision and blinding sensitivity has relatively small dimensions and can be operated in a normally illuminated room. The filter 8 which is arranged in front of the opening 7 can reduce the light which enters from outside into the apparatus and the eyes of the tested person.

Although a particular preferred embodiment of the invention has been disclosed in detail for illustrative purposes, it will be recognized that variations or modifications of the disclosed apparatus, including the rearrangement of parts, lie within the scope of the present invention.

The embodiments of the invention in which an exclusive property or privilege is claimed are defined as follows:

1. In an apparatus for testing twilight vision and blinding sensitivity, including a screen which is illuminated simultaneously by first and second projectors, a test figure being arranged in the beam of the first projector and including means for controlling the light intensity from both projectors with respect to one another so that the light intensity from the first projector increases in the same degree as the light intensity from the second projector is decreased and vice versa, and including a headlight source arranged next to the field of vision on the screen, the improvement comprising wherein the screen is arranged at the focal point of a concave mirror, wherein between the concave mirror and the screen there is arranged a semi-transparent mirror which is inclined with respect to the optical axis of the concave mirror, which semi-transparent mirror is opposite the eyes of the tested person, wherein the apparatus has an opening along the line of sight of the tested person which permits an unhindered looking out, and wherein the opening is provided with a filter for reducing the light entering from outside.

2. The apparatus according to claim 1, including at least one fixation point which lies next to the image of the test figure on the screen and is projected onto the screen by a further projector.

3. The apparatus according to claim 1 or claim 2, including two further filters which can each be arranged in the beam of a respective one of the first and second projectors.

4. The apparatus of claim 3, including a pair of rotationally supported disks and a plurality of said further filters supported at peripherally spaced locations on each said disk, rotation of each said disk effecting successive alignment of said filters supported thereon in the beam of a respective one of said first and second projectors.

5. The apparatus of claim 2, wherein each said projector includes at least one mirror which deflects the beam of light from the lamp of the projector toward said screen.

6. The apparatus of claim 2, wherein each said projector includes two mirrors, the beam of light from the lamp of each projector traveling in a first direction to one said mirror, being deflected by said one mirror and traveling in a second direction to a second said mirror, and being deflected by said second mirror toward said screen.

* * * * *